US010919054B2

(12) United States Patent
Moser et al.

(10) Patent No.: US 10,919,054 B2
(45) Date of Patent: Feb. 16, 2021

(54) METHOD OF EMITTING A WATER JET AND NOZZLE ELEMENT FOR PERFORMING THE METHOD

(71) Applicant: MEDAXIS AG, Baar (CH)

(72) Inventors: Beat Moser, Uerzlikon (CH); Adrian Zweifel, Jona (CH); Beat Widmer, Lucerne (CH); Matthias Widmer, Zug (CH)

(73) Assignee: Medaxis AG, Baar (CH)

( * ) Notice: Subject to any disclaimer, the term of this patent is extended or adjusted under 35 U.S.C. 154(b) by 43 days.

(21) Appl. No.: 15/165,994

(22) Filed: May 26, 2016

(65) Prior Publication Data

US 2016/0346794 A1 Dec. 1, 2016

(30) Foreign Application Priority Data

May 29, 2015 (EP) .................................... 15169900

(51) Int. Cl.
*B05B 1/04* (2006.01)
*B05B 9/04* (2006.01)
(Continued)

(52) U.S. Cl.
CPC ............ *B05B 1/04* (2013.01); *A61B 17/3203* (2013.01); *B05B 9/0403* (2013.01); *B08B 3/026* (2013.01); *B08B 2203/02* (2013.01)

(58) Field of Classification Search
CPC .... B05B 1/04; B05B 1/02; B05B 1/06; B05B 1/048; B05B 9/0403; B08B 3/026; B08B 3/028; B08B 2203/02; A61B 17/3203
(Continued)

(56) References Cited

U.S. PATENT DOCUMENTS 3,437,274 A * 4/1969 Apri ..................... B05B 1/042
239/599
4,806,172 A * 2/1989 Adaci ..................... B08B 3/028
134/34
(Continued)

FOREIGN PATENT DOCUMENTS

CN 101983038 A 3/2011
CN 102648866 A 8/2012
(Continued)

OTHER PUBLICATIONS

European Patent Office, European Search Report issued in priority application No. EP 15169900.6. dated Jul. 20, 2015.
(Continued)

*Primary Examiner* — Tuongminh N Pham
(74) *Attorney, Agent, or Firm* — Fishman Stewart PLLC

(57) ABSTRACT

A method of emitting a water jet includes emitting a water pressure between 50 and 200 bar through a nozzle element that has a cylindrical nozzle body forming a flow passage for the water jet, and at least one nozzle opening emitting a jet stream to the surrounding area whose smallest dimension is not more than 0.15 mm, and wherein a fan jet is created on the surface to be treated at a working distance of about 80 mm between the nozzle opening and the surface to be treated. A handpiece is disclosed that includes a nozzle element that may be accommodated in the handpiece and may, in part, provide for emitting a water jet as disclosed.

18 Claims, 7 Drawing Sheets

(51) Int. Cl.
*A61B 17/3203* (2006.01)
*B08B 3/02* (2006.01)

(58) Field of Classification Search
USPC ....... 239/554, 555, 596, 590, 589, 601, 599; 604/70
See application file for complete search history.

(56) References Cited

U.S. PATENT DOCUMENTS

| | | | |
|---|---|---|---|
| 6,158,679 A * | 12/2000 | Ohmi | G01F 1/40 239/589 |
| 6,375,635 B1 | 4/2002 | Moutafis et al. | |
| 6,960,182 B2 | 11/2005 | Moutafis et al. | |
| 7,122,017 B2 | 10/2006 | Moutafis et al. | |
| 7,905,895 B2 | 3/2011 | Pein | |
| 8,062,246 B2 | 11/2011 | Moutafis et al. | |
| 2002/0111579 A1 | 8/2002 | Moutafis et al. | |
| 2002/0176788 A1 | 11/2002 | Moutafis et al. | |
| 2002/0177802 A1 | 11/2002 | Moutafis et al. | |
| 2004/0098989 A1 * | 5/2004 | Mansour | B05B 7/0458 60/775 |
| 2004/0243157 A1 | 12/2004 | Connor et al. | |
| 2005/0159765 A1 | 7/2005 | Moutafis et al. | |
| 2006/0076438 A1 * | 4/2006 | Dallmeyer | F02M 51/005 239/585.1 |
| 2006/0264808 A1 | 11/2006 | Staid et al. | |
| 2007/0075158 A1 * | 4/2007 | Pelletier | B05B 1/3436 239/11 |
| 2007/0095948 A1 * | 5/2007 | Onishi | F02M 61/1853 239/533.12 |
| 2008/0221602 A1 | 9/2008 | Kuehner et al. | |
| 2010/0049228 A1 | 2/2010 | Kuehner et al. | |
| 2010/0286636 A1 * | 11/2010 | Braendli | A61B 17/3203 604/310 |
| 2011/0002562 A1 | 1/2011 | Chen | |
| 2011/0028887 A1 * | 2/2011 | Fischer | A61B 17/3203 604/22 |
| 2011/0150680 A1 | 6/2011 | Dion et al. | |
| 2012/0172874 A1 | 7/2012 | Fischer et al. | |
| 2012/0221027 A1 | 8/2012 | Kojima et al. | |
| 2014/0079580 A1 | 3/2014 | Habe | |
| 2014/0107620 A1 * | 4/2014 | Fech | A61M 25/0067 604/518 |

FOREIGN PATENT DOCUMENTS

| | | |
|---|---|---|
| DE | 19928441 A1 | 12/2000 |
| DE | 202004014104 U1 | 12/2004 |
| DE | 2015032866 A1 | 3/2015 |
| EP | 1621152 A1 | 2/2006 |
| EP | 2251142 A1 | 11/2010 |
| JP | S54-60448 | 5/1979 |
| JP | S56130338 A | 10/1981 |
| JP | S-29695 Y2 | 3/1990 |
| JP | H5-190720 A | 7/1993 |
| JP | 2002543913 A | 12/2002 |
| JP | 2004353661 A | 12/2004 |
| JP | 2006517832 A | 8/2006 |
| JP | 2011092759 A | 5/2011 |
| JP | 2011516131 A | 5/2011 |
| JP | 2012176159 A | 9/2012 |
| JP | 2015-062733 A | 4/2015 |
| WO | 2004014660 A2 | 2/2004 |
| WO | 2015032866 A1 | 3/2015 |

OTHER PUBLICATIONS

Japanese Office Action, 2016-107318, dated Jun. 6, 2017.
Chinese Office Action, 201610367796.3 dated Apr. 10, 2018.
Japanese Office Action, 2016-107319, dated Sep. 3, 2019 (with English translation).
English Abstract for JP2004353661.
English Absract for JPH05-190720A.

* cited by examiner

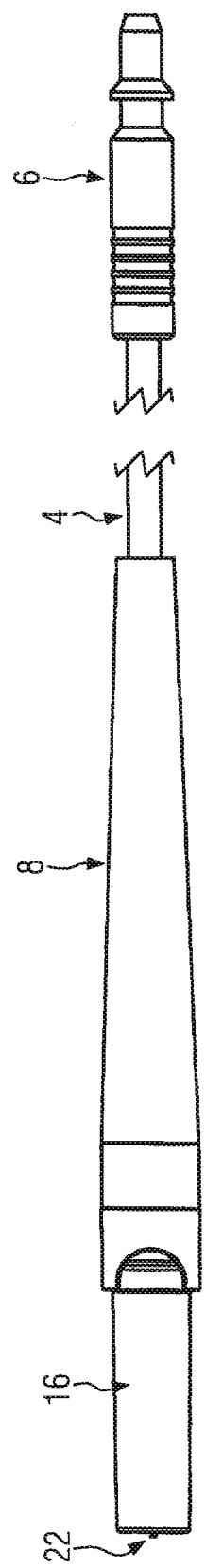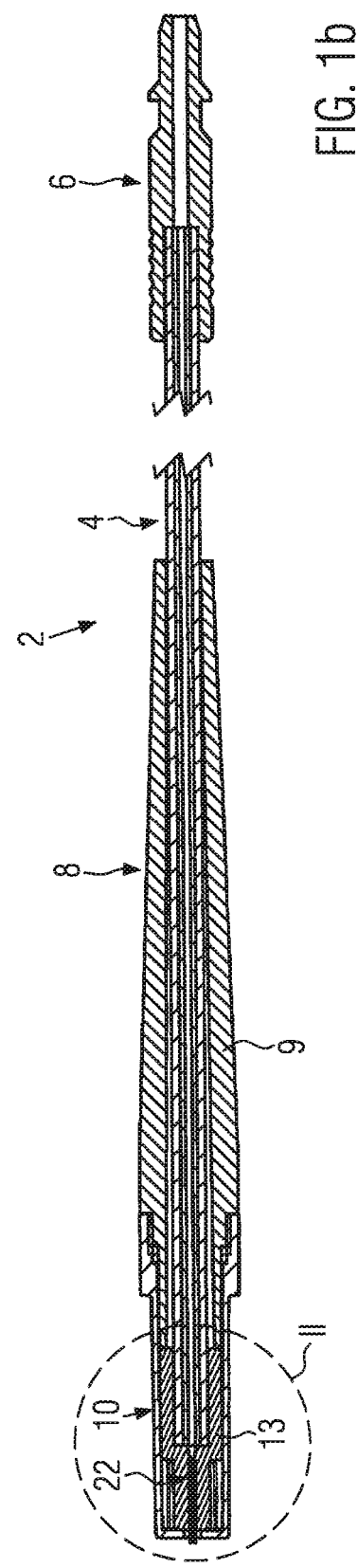

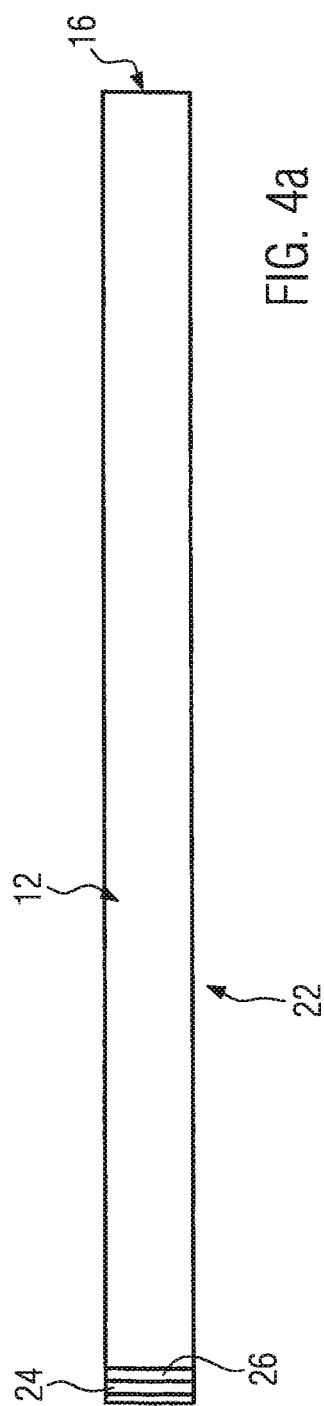
FIG. 4a
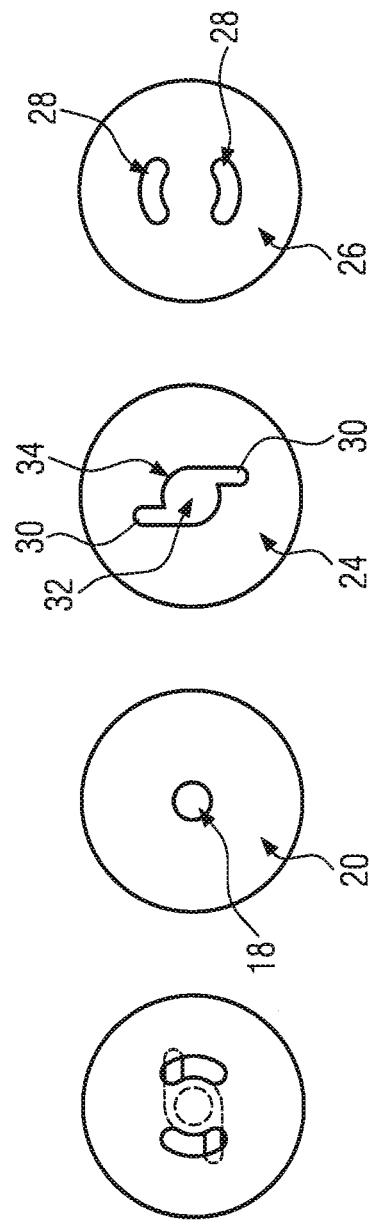
FIG. 4b
FIG. 4c
FIG. 4d
FIG. 4e

METHOD OF EMITTING A WATER JET AND NOZZLE ELEMENT FOR PERFORMING THE METHOD

CROSS-REFERENCE TO RELATED APPLICATION

This application claims the benefit of priority to European patent application No. 15169900.6, filed May 29, 2015, which is incorporated herein by reference in its entirety as though fully set forth herein.

TECHNICAL FIELD

The present invention relates to a method of emitting a water jet at a water pressure between 50 and 200 bar.

BACKGROUND

Pressure washers for emitting water onto a surface to be treated have been well-known for a long time. Such methods are usually performed in industry and home applications with pressure washers including a handle provided with a control button by which the high-pressure jet may be switched on and off. The high-pressure jet is applied to the surface to be treated as extensively as possible. In this respect, there is a target conflict between a focused hard jet and an appropriate size of the jet in order to achieve the desired success when the jet once passes over the surface to be treated.

The present invention intends to approach a new method of emitting a water jet for treating a surface. In this respect, the present invention is guided by the idea that even sensitive surfaces must be treated by means of a water jet, for example to treat organic surfaces, clean tissue, and loosen and remove incrustations located thereon. This may be employed for cosmetic or medical reasons. The method is to be employed in particular for debridement.

Furthermore, the present invention intends to provide a device suited for performing the method.

SUMMARY

For achieving the object in terms of the method, the present invention provides a method of emitting a water jet onto a surface to be treated having the features of claim 1. Emission is effected at a water pressure between 50 and 200 bar, preferably between 60 and 130 bar. This water pressure is typically set at the pump side. In the method according to the invention, the water jet is emitted through a nozzle element having a cylindrical nozzle body. The latter forms a flow passage for the water jet. Furthermore, the nozzle element includes a nozzle opening which emits the jet stream to the surrounding area. The above mentioned water pressure is usually also applied as back pressure within the nozzle body and, in the direction of flow, directly in front of the nozzle opening. For performing the method, the nozzle opening is selected to be relatively small to apply the water jet onto the surface to be treated at a manageable jet impact pressure. In the method according to the invention, the smallest dimension of the nozzle opening is not more than 0.15 mm, preferably not more than 0.13 mm, and at least 0.02 mm. The smallest dimension is considered as the diameter in case of a circular opening, as the smallest diameter in case of an oval opening, and as the width in case of an oblong nozzle opening. The nozzle opening preferably has an opening surface of not more than $1.8 \cdot 10^{-2}$ mm$^2$, preferably between $4.6 \cdot 10^{-3}$ mm$^2$ and $1.3 \cdot 10^{-2}$ mm$^2$. The nozzle opening, optionally also the geometry of the flow passage preceding the nozzle opening, is selected such that a fan jet is formed on the surface to be treated at a distance of 80 mm between the nozzle opening and the surface to be treated. A fan jet in the sense of the present invention is understood to be a jet whose length-to-width ratio is at least 2.5. Typically, the ratio of length to width of the fan jet is between 2.5 and 15, preferably between 4 and 10. This length ratio is fulfilled by the jet impact pressure range of the fan jet impacting the surface required for the treatment. Any drops or mist released from the surface of the jet at the jet due to surface effects and impacting the surface to be cleaned with an insufficient impulse at said working distance are not considered in this length ratio.

With the method according to the invention, it is possible to clean relatively sensitive surfaces with a water jet. The water jet may be provided with cleaning additives. Such cleaning additives may also be antibacterial additives by which bacteria on the surface to be cleaned are killed. Optionally, a light ray may also be applied in addition which emits waves within a sterilizing range and is typically emitted essentially in parallel to the water jet, preferably emitted from a handpiece which accommodates the nozzle element and simultaneously comprises a light emission aperture. The light source may be provided in the handpiece. As an alternative, the emitted light may also be supplied to the handpiece via a light conductor. The light source preferably emits light at a wavelength in the ultraviolet range. Such a method procedure is suited, for example, for the cosmetic treatment of skin to remove impurities and optionally kill bacteria.

According to a preferred development of the present invention, a jet impact pressure of at least 1,000 Pa and preferably not more than 60,000 Pa is created at said working distance of 80 mm on a surface area of at least 3 mm$^2$ of the surface to be treated. If the stated upper limiting value for the jet impact pressure is exceeded, a non-acceptable impairment of the surface to be treated is expected in the method according to the invention. Below said jet impact pressure, the effect to be achieved by the treatment is no longer achieved to the desired degree. The stated surface area here corresponds to the requirement of a cleaning of the surface to be cleaned over a sufficiently large area. The jet impact pressure is the pressure that impacts the surface to be treated from the component of the pulse force at right angles and is measured. Preferred higher minimum limits for the pressure acting within the surface area are 5,000 Pa or 10,000 Pa, respectively. Preferred lower maximum limits for the pressure acting within the surface area are 40,000 Pa and 35,000 Pa, respectively. In view of a manageable surface to be treated, the surface area should preferably not exceed 100 mm$^2$, particularly preferred 50 mm$^2$, more particularly preferred 20 mm$^2$, and even more preferred 12 mm$^2$.

Practical tests by the applicant showed that the fan jet possibly splits on its way between the nozzle opening and the surface to be treated, and includes, for example, two, optionally also several regions with a relatively high jet impact pressure which enclose regions with a low jet impact pressure between them, where this jet impact pressure does not show sufficient effects at the surface to be treated. Here, the effect of the jet on the surface is in any case not affected if the jet impact pressure considered to be necessary for a sufficient effect is located externally around a region of the jet impact pressure profile of the surface to be treated which includes a region with lower jet impact pressure values. Thus, according to a preferred development of the present invention, and in view of an economical treatment of the surface, it is suggested to create a jet impact profile on the surface to be treated which has a homogenous, continuous, oblong and preferably linear design.

Practical tests furthermore showed that for forming a fan jet by means of a spray medium which has a similar viscosity and surface tension as water within a temperature range between 20 and 40° C., it is advantageous to observe certain Reynolds' numbers for the flow within the nozzle body, i. e. in the flow passage and the nozzle opening. The suggestion made in the subclaims in this respect is guided by a pressure range between 50 and 200 bar for the water pressure at room temperature.

If in this preferred pressure and temperature range, a jet treatment of the surface by means of a suited spray medium is generated under the influence of atmosphere, a fan jet with the desired atomization may be generated with high accuracy. Thus, the present invention suggests to set the Reynolds' number in the flow passage on the inlet side between 450 and 28,000, and on the outlet side at about 3,900 to 46,000. The corresponding Reynolds' numbers may be precalculated by fluid-dynamic analyses with reference to the geometry and the corresponding boundary conditions. For generating the fanning out of a jet into a fan jet, the radial speed component at the nozzle outlet is decisive. When precalculating the flow properties acting in the method according to the invention, the applicant has performed numerical flow calculations and found out that the anisotropy of turbulence is important in particular for open jet simulations. For these calculations, the Reynolds stress turbulence model BSL by Ansys CFX 14.5 was helpful. The model as such is described, for example, in (ANSYS® Academic Research, Release 14.5, Help System, Solver Modeling Guide, ANSYS, Inc.). For the flow in the nozzle body and in the nozzle opening, the SST turbulence model by Ansys CFX 14.5 was employed. By means of this model, the radial speed component by which the jet pattern may be estimated may be reliably determined. By means of appropriate models, the atomization processes may also be detected which dissolve the compact jet and create the desired jet impact pressure even at a relatively small working distance of 80 mm.

According to current considerations, the flow conditions that are adjusted in the direction of flow upstream of the nozzle body are also important. The nozzle body typically has a length of between 1 and 30 mm, preferably between 1 and 10 mm. The diameter of the flow passage typically provided with a round cross-section may be between 0.15 and 0.6 mm, preferably between 0.25 and 0.35 mm, particularly preferred 0.3±0.05 mm. This nozzle body is typically accommodated in a handpiece which forms an intermediate conduct leading to the flow passage.

The transition between the flow passage and the nozzle opening is preferably unsteady. Thus, tests by the applicant showed that a preferred influence of the jet as a fan jet is possible by the nozzle opening being strictly cylindrical. The flow passage upstream of the nozzle opening is also preferably strictly cylindrical. Accordingly, the nozzle opening is provided in a shield that terminates the flow passage. Preferably, the nozzle opening is provided concentrically to the flow passage. Such an embodiment also allows for an inexpensive manufacture of the nozzle element suggested for performing the method by the independent of the present invention. The nozzle element according to the invention is stated in claim 7.

Insofar as the performance of the method and the particular conditions within the nozzle element and the properties of the fan jet were discussed above, these developments equally apply for the nozzle body. While the method may be performed within the above mentioned pressure interval of between 50 and 200 bar, a pressure range between 50 and 130 bar is to be preferred for performing the method.

According to a preferred development of the present invention, the jet is emitted through a nozzle opening embodied as a sheet nozzle and applied onto the surface to be treated as a fan jet with an orientation offset with respect to the longitudinal extension of the sheet nozzle approximately at right angles. The jet is thus reoriented in the air gap between the nozzle opening and the surface to be treated.

For characterizing the nozzle element according to the invention, however, a water pressure of 130 bar is considered. Nozzle elements which show the above discussed jet impact pressures (minimum and maximum) and jet impact pressure profiles on the surface to be treated at the mentioned working distance of 80 mm at such a system pressure or such a pressure within the flow passage are developments of the nozzle element according to the invention. It showed that a plurality of nozzle elements may be created by means of fluid-dynamic precalculation and analysis. Thus, the present invention mainly defines the nozzle element according to the invention by means of the parameters that characterize the created fan jet under the mentioned conditions (water pressure 130 bar, working distance 80 mm).

The nozzle element of the present invention is accordingly preferably designed such that, at a working pressure of 130 bar and a working distance between the nozzle opening and the surface to be treated of 80 mm, it forms a fan jet having the features of claims 1, 2 and 6 on the surface to be treated. The nozzle element according to the invention is furthermore preferably embodied such that, at a pressure of 130 bar, flow conditions in the nozzle element occur according to the Reynolds' numbers according to claim 3. The nozzle element is preferably used for debridement, and thus the use of the nozzle element specified here is also claimed for debridement. The nozzle according to the invention may be manufactured much more easily and thus inexpensively than the nozzle already known, for example, from EP 2 251 142 A1. Moreover, this already known nozzle does not produce a fan jet. Irrespective of this, the development according to claim 6 for such a nozzle element is considered per se to be essential for the invention for debridement. For this, it is not necessary for the nozzle element to be embodied and suited for generating a fan jet on the surface. Already the welding of the nozzle plate to the nozzle body may be per se essential for the invention.

The unsteady transition between the nozzle opening and the flow passage may be quite easily achieved in terms of production by the nozzle body being made of metal, in particular steel, and the nozzle plate being welded to the nozzle body. Both the nozzle body and the nozzle plate are usually made of the same material. The nozzle opening may be cut by means of laser or be formed photolithographically or by means of etching. The nozzle element may be a consumable part, so that the nozzle element is discarded after the first use. This is in particular essential if hygienic boundary conditions are decisive or the nozzle element and/or the handpiece are contaminated at first use and may not be reused. Hygienic conditions may also be relevant in the treatment of biological surfaces. Thus, the nozzle body should be inexpensive to manufacture which is ensured with said welding of a basically cylindrical nozzle body with a pin aperture as nozzle plate. The two components are usually welded by front-side laser welding against the surface of the nozzle plate. Such welding results in a fluid-tight connection between the nozzle plate and the nozzle body.

As already mentioned, the nozzle opening is preferably embodied as sheet nozzle. The ratio of the length of the sheet nozzle to the width of the sheet nozzles, i. e. the length-to-width ratio, should be between 1 and 7, preferably between 3 and 4. The length is here understood as the longest extension of the sheet nozzle. The width is the extension in one direction at a right angle thereto each in a plane which is orthogonally penetrated by the flow within the nozzle. In other words, the ratio is the design of the nozzle's cross-section. The width of the sheet nozzle is between 0.035 and 0.06 mm, preferably between 0.04 and 0.055 mm.

The applicant has performed systematic examinations concerning different nozzle geometries. In these examinations, cross-recess nozzles and also nozzles with a broad, but non-linear cross-section were examined. Moreover, elliptic nozzles and nozzle plates with several bores, for example provided in a row next to one another, were examined. It turned out that the flow conditions discussed above are at least as relevant for the formation of a relatively small fan jet at the desired working distance as the geometric design of the nozzle.

It furthermore showed that a sheet nozzle whose nozzle opening includes straight main side walls and concavely curved side walls, where the radius of curvature corresponds to at least half the width of the nozzle opening and which is not larger than 0.15 mm, creates a very good fan jet. In this embodiment, the main side walls extend in parallel and straightly with respect to each other. They end in a concave curvature. The radius of the curvature is at least half the width of the sheet nozzle. The radius is at most 0.15 mm. In view of the preferred flow conditions, the nozzle opening should be provided regularly offset to the inner circumference of the flow passage, so that the desired unsteadiness between the flow passage and the nozzle opening is given.

It surprisingly also showed that a fan jet may be created with a circular nozzle opening having a diameter between 0.09 mm and 0.12 mm. The same is also possible with a corresponding mean oval diameter, the smallest diameter of the oval being preferably between 0.08 and 0.11 mm, and the larger diameter of the oval not exceeding 1.3 times the smallest diameter. Here, the fan jet may be preferably formed by at least one shield plate being disposed upstream of the nozzle plate in the direction of flow, where the shield opening is larger than the nozzle opening. The shield opening should, however, have a nozzle area of not more than 150% of the nozzle area of the nozzle opening. In case of a rotationally symmetric nozzle opening, the shield opening should be embodied and disposed not rotationally symmetrically, but concentrically to the center of the nozzle opening. Moreover, the shield opening is preferably strictly cylindrical, so that the walls defining the shield opening extend at right angles to the inner or outer surfaces of the shield plate forming the shield. With a circular nozzle opening, the shield opening may be embodied, for example, to be oval or to be an oblong hole, wherein the oblong hole is only slightly wider than the diameter of the shield opening. The width of the oblong hole should be larger than the diameter of the nozzle opening by two to five hundredth millimeters.

According to a further preferred embodiment of the present invention, two shield plates are provided upstream of the nozzle plate in the direction of flow. As in the above described embodiment, each individual plate is preferably connected to the layer underneath by means of laser welding. The first plate in the direction of flow is accordingly welded to the nozzle body, the plate following in the direction of flow to the plate underneath, etc. The shield plates provided one behind the other in the direction of flow usually have different shield openings. The shield openings are preferably provided so as not to be rotationally symmetric to the longitudinal center line of the nozzle opening, i. e. the center of a circular nozzle opening, however shaped or arranged point-symmetrically to this point or to this axis. Thereby, a torsion may be imparted to the flow when it exits from the nozzle element. Thus, the first shield plate in the direction of flow may be provided with two or more shield openings being opposite with respect to each other and having a basically annular segment design. A second shield plate may follow these two shield openings which has a central circular shield opening from which slots originate which flush with the annular segment-like shield openings. The respective plates should have a thickness of between 0.06 and 0.20 mm.

The present invention furthermore suggests a hose element with a fluid hose which is provided at one inlet end with a connection element for connecting the hose element to a pump, and at its outlet end with a handpiece. The handpiece is connected at the end side to the above described nozzle element according to one of the above discussed claims. This hose element may be pre-assembled as a tradeable unit which is in particular recommended if the nozzle element is difficult to handle due to its small size. The nozzle element may be glued into the above mentioned handpiece. As an alternative, the nozzle element may also be clamped between one handpiece main body and an end cap which is releasably connected to the handpiece main body, for example via a bayonet or screw connection. Here, the end cap grips over the nozzle body and presses the latter preferably against a locating shoulder which limits the intermediate conduct at the side of the flow outlet.

The present invention furthermore suggests a handpiece for such a hose element. The handpiece is characterized in that it may also be manufactured and distributed without the fluid hose of the hose element to be later connected to any hose element by the user. To this end, the handpiece according to the invention includes a handpiece main body which comprises an oblong bore suited for passing through the fluid hose. The handpiece main body is usually shaped according to ergonomic aspects, so that it may be held between the fingers of a hand. The handpiece main body is usually slim, oblong and embodied with a rotationally symmetric cross-section. The handpiece main body comprises an end cap at the end side. The latter is usually releasably connected to the handpiece main body. The end cap in any case encloses an adapter piece between itself and the handpiece main body. This adapter piece is usually made of plastics and carries the above mentioned nozzle element which is preferably made of metal. This nozzle element is usually glued to the adapter piece. The adapter piece always has a bore for receiving the nozzle element. Moreover, connection means for a sealing connection of the fluid hose to the adapter piece are always provided. In a simple embodiment, the adapter piece includes a bore in which the fluid hose is inserted with its free end and may be there connected to the adapter piece in a fluid-tight manner. In a simple embodiment as a disposable product, the fluid hose is also glued to the adapter piece.

Here, the nozzle element is preferably received in the adapter piece such that the nozzle element projects beyond the adapter piece with its free end. Correspondingly, the nozzle element usually also projects beyond the end cap gripping over the nozzle element on the front side, so that the nozzle element slightly projects with respect to this nozzle cap. The end cap usually has a bore which is penetrated by the nozzle element. However, the bore usually leaves a sufficient radial distance to the front end of the nozzle element. It is mainly essential that the end cap grips over the adapter piece on the end side and fixes the adapter piece in the axial direction in the handpiece, usually by screwing the end cap against the handpiece main body in the axial direction.

The present invention finally relates to a method for manufacturing a nozzle body in which at least one nozzle opening is embodied at a nozzle plate by means of laser welding. The nozzle plate is cut out of a nozzle plate sheet, wherein connection webs are left between the nozzle plate, which is connected to the nozzle body by means of laser welding, and the plate piece. Thus, the relatively small nozzle plate may be placed over the piece of sheet and positioned. Then, the nozzle plate is welded to the nozzle body. In the process, the remaining connection webs are separated to isolate the nozzle plate connected to the nozzle body from the semi-finished product. The beam used for welding is correspondingly also used for cutting the connection webs.

The present invention will be illustrated more in detail below with reference to exemplified embodiments in connection with the drawings.

DESCRIPTION OF THE DRAWINGS

In the drawings:

FIGS. 1a and b show a long-side or longitudinal section of an exemplified embodiment of a hose element;

FIG. 3b shows a plan view of the front nozzle plate 20 according to FIG. 3a;

FIG. 3c shows a plan view of the rear nozzle plate 24 according to FIG. 3a;

FIG. 4a shows a side view of a second exemplified embodiment of a nozzle element;

FIGS. 4b-4d show plan views of nozzle and shield plates of the second exemplified embodiment;

FIG. 4e shows a plan view of the sheets of FIGS. 4b-4d provided one behind the other;

DETAILED DESCRIPTION

Figure 2:
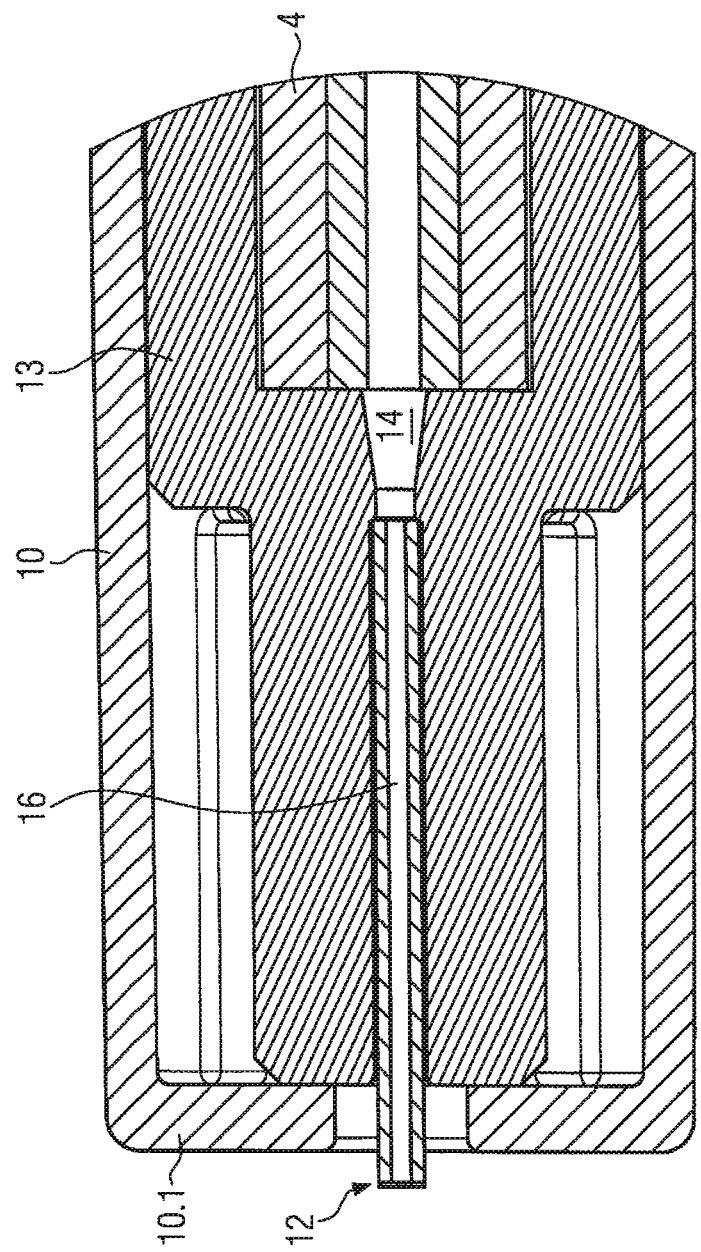
FIG. 2 shows the detail designated with II in FIG. 1b in an enlarged representation.
Figure 3A:
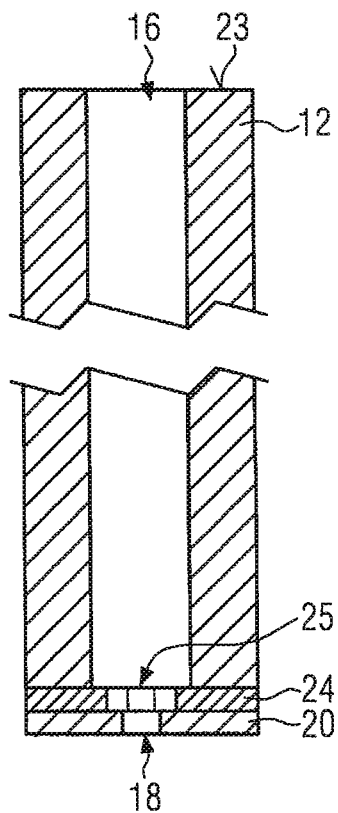
FIG. 3a shows a longitudinal section of a first exemplified embodiment of a nozzle element.
Figure 3D:
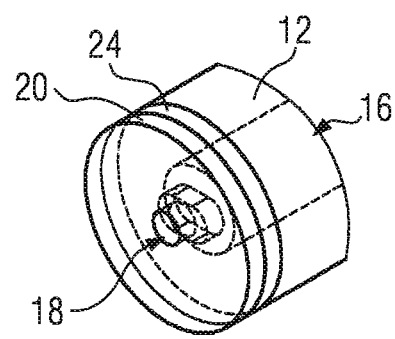
FIG. 3d shows a perspective front view of the first exemplified embodiment.
Figure 3B:
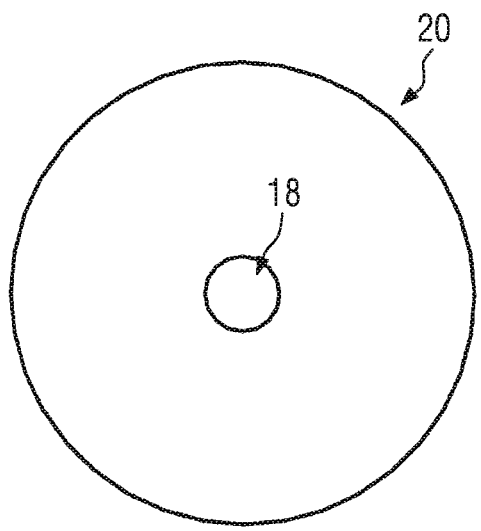
Figure 3C:
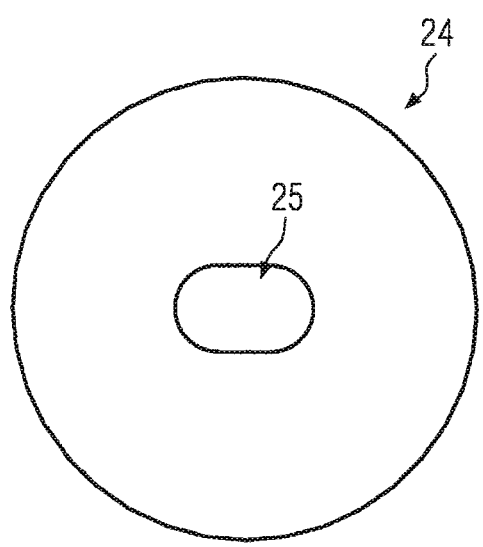

FIG. 1 shows a plan view of a hose element 2 with a flexible fluid hose 4 which has an inner diameter of 0.8 mm and an outer diameter of 4 mm. At the end of the fluid hose 4 where it is fixed, there is a hose coupling 6 which is embodied as detachable coupling, e.g. with a bayonet safety device for fixing it to an outlet piece at a non-depicted pump. At its opposite end, the fluid hose 4 is provided with a handpiece 8 which is formed of a handpiece main body 9 and an end cap 10 which is connected at the end side with the handpiece main body 9 and encloses an adapter piece 13 holding the nozzle body 12. For this, the handpiece main body 9 comprises, at the front side, an external thread which is screwed onto the end cap 10. As is shown in FIG. 2, the end cap 10 has a front-side end face 10.1 which abuts the adapter piece 13 at the front side and fixes the latter in the handpiece 8 and comprises a central bore through which the nozzle body 12 extends and which surrounds the front end of the nozzle body 12 with sufficient clearance. At the opposite ends, the hose coupling 6 is glued to the fluid hose 4.

The handpiece 8 forms an intermediate conduct which is embodied in the present case as a conical transition conduct in the adapter piece 13. The end of said intermediate conduct 14 on the side of the hose has a diameter larger than the flow diameter of the fluid hose 4. Downstream of the intermediate conduct 14, the adapter piece 13 has a bore adapted to the outer diameter of the fluid hose 4 in which the fluid hose 4 is glued to the adapter piece 13. The handpiece main body 9 has a continuous receiving bore for the fluid hose 4 in which the fluid hose 4 is held with clearance and which is embodied such that the fluid hose 4 may be easily pushed through this bore. The downstream end of the intermediate conduct 14 is cylindrical. There, the intermediate conduct 14 passes over into a flow passage 16 which is formed by the nozzle body 12 and leads to a nozzle opening 18 which is represented in the following figures each and is recessed at a nozzle plate 20 by means of laser welding. The metallic nozzle body 12 is inserted in a bore of the adapter piece 13 adapted with its inner circumference to the outer circumference of the nozzle body 12. The nozzle body 12 is glued to the adapter piece 13 inside this bore. The flow passage 16 has a cross-section of flow which is considerably smaller than the downstream diameter of the intermediate conduct 14. In this way, it is securely prevented that glue possibly pressed out of the gap between the two circumferential surfaces of the nozzle body 12 and the adapter piece 13 during the joining process conglutinates the flow passage 16 on the inlet side. The adapter piece 13 is usually made of plastics. The end cap 10 may be formed of plastics or metal. The proximal end of the fluid hose 4 is also glued to the hose coupling 6.

For manufacturing the exemplified embodiment shown in FIGS. 1 and 2, the fluid hose 4 is usually pushed through the handpiece 8, so that the free end of the hose piece projects beyond the handpiece main body 9. An intermediate product prepared by gluing together the adapter piece 13 and the nozzle body 12 is then placed onto the fluid hose 4 at the end side and glued to the fluid hose 4. Then, the fluid hose 4 is retracted into the handpiece main body 9 to place the adapter piece 13 against the handpiece main body 9 at the front side and secure this position by screwing on the end cap 10.

As already mentioned, the nozzle plate 20 is basically cut out of a semi-finished sheet plate with a circular base by means of laser cutting. Here, radial webs are left which also hold the nozzle plate prepared with the nozzle opening at the larger semi-finished plate. Thus, the relatively small nozzle plate 20 may be positioned with the semi-finished plate. Then, the nozzle plate 20 is welded to the nozzle body 12, the radial webs are simultaneously separated, so that the nozzle plate 20 with a circular outer circumference is present and continues the cylindrical outer circumference of the nozzle body 12 in a flush manner and without shoulders. Thus, a nozzle element designated with reference numeral 22 is created.

The figures illustrated below show exemplified embodiments of the nozzle bodies or nozzle plates.

FIGS. 3a to 3d show a first exemplified embodiment with a cylindrical nozzle body 12 with the flow passage 16, which in the present case has a diameter of 0.3±0.05 mm and is circular. At the inlet side, the nozzle body 12 has a locating surface 23 for abutment against a ring surface formed by the adapter piece 13. The opposite end of the nozzle body 12 is occupied by two steel plates having a thickness of 0.7 mm each. Here, a first shield plate designated with reference numeral 24 is welded to the nozzle body 12 at the front side. The shield plate 24 has an oblong hole 25 with a width of 0.13 mm and a length of 0.21 mm. The indications include work tolerances of 0.005 mm and may vary by ±0.03 mm without departing from the concept presented here. The nozzle plate designated with reference numeral 20 has a circular cylindrical nozzle opening 18 with a diameter of 0.114 mm. This nozzle opening 18 is arranged and embodied to be concentric to the center of the oblong hole 25. The two openings 18, 25 comprise parallel inner walls which are embodied and oriented at right angles to the front and rear surfaces of the respective plates. Thus, shoulders result on the one hand between the outer circumference of the flow passage 16 and the shield opening designated with reference numeral 25 on the one hand and this shield opening 25 and the nozzle opening 18. The nozzle plate 20, too, is welded to the shield plate underneath by means of laser welding. Welding is effected in each case at the front side. The weld seam is welded continuously.

FIGS. 4a to 4e illustrate a second exemplified embodiment with a nozzle plate 20 (FIG. 4d) which has a circular nozzle opening 18 which is preceded by two shield plates 24 (FIG. 4c) and 26 (FIG. 4b) in the direction of flow. Here, the first shield plate 26 shown in FIG. 4b is directly welded to the nozzle body 12. The second shield plate 24 is directly welded onto this first shield plate 26. The nozzle plate 20 is in turn welded onto the second shield plate 24. FIG. 4e shows a plan view of the first shield plate 26 through the flow passage 16. As can be seen, the two annular segment-shaped recesses 28 provided at the first shield plate 26 flush with slot-like extensions 30 which originate from a central bore 32 of a shield opening 34 recessed in the second shield plate 24. This central bore 32 in turn flushes with the nozzle opening 18. The two shield plates 24, 26 have a thickness of 0.1 mm. The nozzle plate 20 has a thickness of 0.07 mm.

By this embodiment, a torsion is imparted to the flow directed through the flow conduct 16 at the end, so that the jet stream is emitted to the surrounding area with a rotary speed component.

Figure 5:
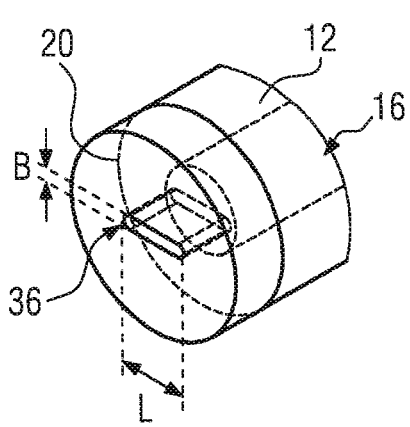
FIG. 5 shows a perspective view of a further exemplified embodiment of a nozzle plate with parts of the nozzle body.

FIG. 5 illustrates a further exemplified embodiment of a nozzle plate 20. The latter is provided with a sheet nozzle 36 in which the nozzle opening 18 has two straight main side walls extending in parallel thereto, and concave front walls. In the present case, the front walls are embodied with a radius corresponding to half the width of the sheet nozzle 36. The width B of the nozzle opening 18 is 0.05 mm. The length L is 0.256 mm. Here, too, the mentioned measures may vary by +/−25% without departing from the concept discussed herein. The nozzle plate 20 has a thickness of 0.20 mm. All recesses and contours are cut by laser. The preferred ratio of length L to width B is between 4.3 and 6.5, in the present case 5.1.

Figure 6:
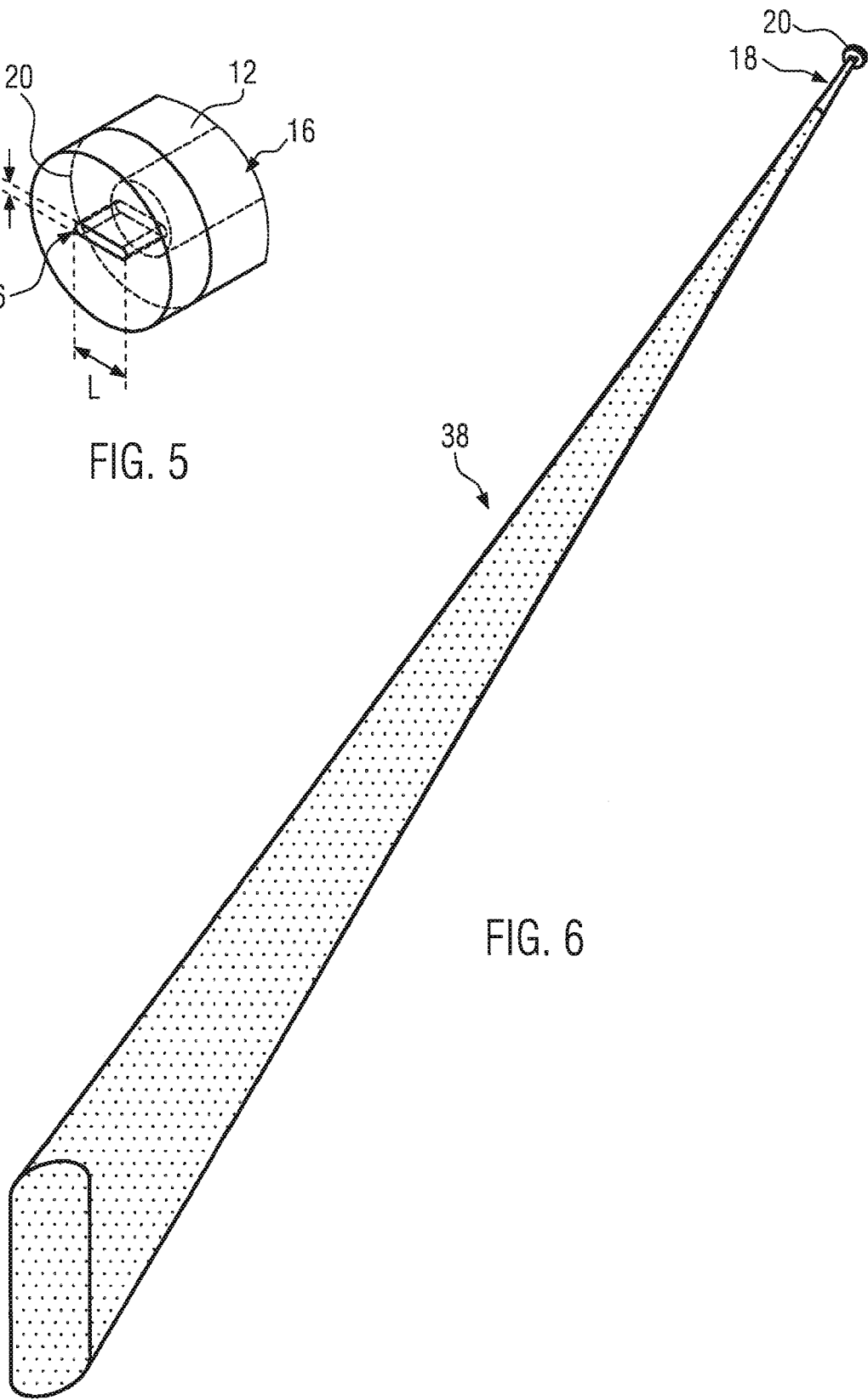
FIG. 6 shows a perspective plan view of a fan jet which is emitted by the shield plate shown in FIG. 5.
Figure 6A:
FIGS. 6a-6c show profiles of the fan jet according to FIG. 6.
Figure 6B:
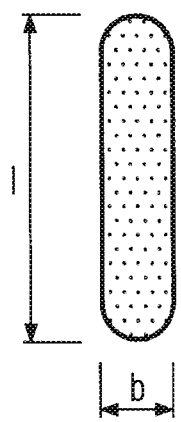

FIG. 6 schematically shows a fan jet 38 which is emitted to the surrounding area by the embodiment of the sheet nozzle 36 discussed with reference to FIG. 5. Here, FIGS. 6a and 6b illustrate sectional views of the fan jet on the one hand at the level of the sheet nozzle 36 (FIG. 6a), and on the other hand at a distance of 80 mm from the sheet nozzle. The view is schematic, wherein the cross-section of the fan jet at the level of the sheet nozzle 36 in FIG. 6a was drawn at a scale 40 times larger than the scale according to FIG. 6b.

Figure 6C:
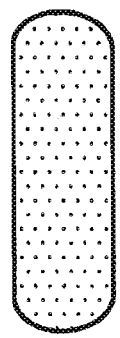

Already FIG. 6 illustrates that the fan jet 38 emitted to the surrounding area is reoriented in the surrounding area, so that, at an assumed horizontal orientation of the fan jet 38 at the level of the sheet nozzle 36, it has a longitudinal extension in the vertical direction at a distance of 80 mm. The width orientation of the fan jet 38 is thus rotated by 90° as is shown in FIGS. 6a and 6b. The cross-sectional shape according to FIG. 6b results for a fan jet which impacts the surface to be treated at an angle of 90°. However, the fan jet is usually inclined relative to this surface. FIG. 6c schematically illustrates the surface of the fan jet 38 which may be used for an effective cleaning of the surface at an orientation of the fan jet at an angle of 45° relative to the surface to be treated.

One can see in FIG. 6 that the developing fan jet has a good width-to-length ratio l/b. A fan jet in the sense of the invention may also have a jet impact pressure profile with convex edges within the effective pressure profile at the working distance. The fan jet 38 impacting on the surface to be treated at a working distance of 80 mm has, within the effective area shown in FIG. 6b, a jet impact pressure of at least 1,000 Pa, a length of 9 mm and a width of 2 mm. Outside these dimensions, the fan jet 28 carries along liquid. However, the jet impact pressure of these outer areas of the fan jet does not show the desired effect on the surface to be treated and is not attributed to the measures of the fan jet of interest here.

The invention claimed is:

1. A nozzle element to be introduced into a handpiece for emitting a water jet with a system water pressure between 50 and 200 bar, the nozzle element comprising:
   a cylindrical nozzle body forming a cylindrical flow passage for the water jet, the cylindrical nozzle body having a length greater than a diameter, which is constant from one end of the nozzle body to the other end, and
   at least one nozzle opening emitting a jet stream to a surrounding area, the at least one nozzle opening having a smallest dimension not more than 0.15 mm and the at least one nozzle opening being formed such that a fan jet is emitted from the at least one nozzle opening toward a surface to be treated between the nozzle opening and the surface to be treated at an impact water pressure of 130 bar at a working distance of 80 mm;
   wherein the nozzle body is a single, integral piece comprised of steel and welded to a nozzle plate, the nozzle plate being welded to an external distal front face of the nozzle body; and
   wherein at least one of:
     the nozzle body has a length of between 1 mm and 30 mm, and the flow passage has a diameter of between 0.15 to 0.6 mm; and
     the nozzle plate has a thickness of between 0.06 mm to 0.2 mm.

2. The nozzle element according to claim 1, wherein the at least one nozzle opening is cylindrical through an entire thickness of the nozzle plate forming the nozzle opening.

3. The nozzle element according to claim 1, wherein a width of the at least one nozzle opening is between 0.035 mm and 0.060 mm.

4. The nozzle element according to claim 1, wherein a width of the at least one nozzle opening is between 0.040 mm and 0.055 mm.

5. The nozzle element according to claim 1, wherein the at least one nozzle opening comprises straight main side walls and has a radius corresponding to at least half the width which is not larger than 0.15 mm and comprises concavely bent front walls.

6. The nozzle element according to claim 3, wherein the nozzle opening is circular with a diameter of between 0.09 and 0.12 mm, or oval with a smallest diameter of the oval between 0.08 and 0.11 mm.

7. The nozzle element according to claim 1, wherein at least one shield plate is preceding the nozzle plate in a direction of flow, and a shield opening of the at least one shield plate is larger than the nozzle opening.

8. The nozzle element according to claim 1, wherein at least two shield sheets are preceding the nozzle plate in the direction of flow which have differing shield openings which are each formed point-symmetrically to a longitudinal central axis.

9. The nozzle element according to claim 7, wherein the shield opening is oblong.

10. The nozzle element according to claim 9, wherein a width of the shield opening is between 0.10 mm and 0.16 mm.

11. The nozzle element according to claim 10, wherein a length of the shield opening is between 0.18 mm to 0.24 mm.

12. The nozzle element according to claim 7, wherein outer diameters of the nozzle plate and the shield plate are the same.

13. The nozzle element according to claim 7, wherein outer diameters of the nozzle plate, the shield plate, and the cylindrical nozzle body are the same.

14. The nozzle element according to claim 7, wherein an inner diameter of the flow passage is larger than a diameter of the nozzle opening and a diameter of the shield opening.

15. The nozzle element according to claim 7, wherein the shield plate is welded to the cylindrical nozzle body, and the nozzle plate is laser welded to the shield plate from a front via a continuous weld seam.

16. The nozzle element according to claim 1, wherein an inner diameter of the flow passage is larger than a diameter of the nozzle opening.

17. The nozzle element according to claim 1, wherein the surface to be treated includes human tissue.

18. The nozzle element according to claim 1, wherein the length of the nozzle body is between 1 mm and 10 mm.

* * * * *